United States Patent [19]

Herbstman et al.

[11] 4,083,800

[45] Apr. 11, 1978

[54] ALKYLATION PROCESS AND METHOD FOR CATALYST REGENERATION

[75] Inventors: Sheldon Herbstman, Spring Valley; John H. Estes, Wappingers Falls, both of N.Y.

[73] Assignee: Texaco Inc., New York, N.Y.

[21] Appl. No.: 746,765

[22] Filed: Dec. 2, 1976

Related U.S. Application Data

[63] Continuation of Ser. No. 604,587, Aug. 14, 1975, abandoned.

[51] Int. Cl.² .................. B01J 21/20; C07C 3/52; C07C 3/56
[52] U.S. Cl. .................. 252/415; 260/683.47; 260/683.53
[58] Field of Search .................. 252/415, 442; 260/683.47, 683.53, 671 R, 666 P

[56] References Cited

U.S. PATENT DOCUMENTS

| | | | |
|---|---|---|---|
| 3,147,229 | 9/1964 | Hinlicky et al. | 252/415 |
| 3,240,840 | 3/1966 | Goble et al. | 260/683.47 |
| 3,440,178 | 4/1969 | Lawrance et al. | 252/415 |
| 3,523,142 | 8/1970 | Mih et al. | 252/442 |
| 3,555,107 | 1/1971 | Estes et al. | 252/442 |
| 3,689,434 | 9/1972 | Suggitt et al. | 252/442 |

*Primary Examiner*—Winston A. Douglas
*Assistant Examiner*—P. E. Konopka
*Attorney, Agent, or Firm*—Thomas H. Whaley; Carl G. Ries; George J. Darsa

[57] ABSTRACT

A process for the alkylation of alkanes with olefins under alkylation conditions employing a regenerated catalyst having improved activity. The regenerated catalyst is prepared by contacting a deactivated chlorided alumina catalyst in a non-oxidizing atmosphere at a temperature between 400° and 1200° F., thereafter contacting said catalyst in an oxidizing atmosphere at a temperature between 700° and 1200° F. and subsequently rechloriding said catalyst at a temperature between 200° and 800° F.

14 Claims, No Drawings

ALKYLATION PROCESS AND METHOD FOR CATALYST REGENERATION

This is a continuation, of application Ser. No. 604,587 filed Aug. 14, 1975, now abandoned.

This invention relates to the alkylation of alkanes with olefins. In particular, this invention relates to the alkylation of isoparaffins with olefins employing a regenerated catalyst which provides an alkylate containing high octane boiling range products.

BACKGROUND OF THE INVENTION

Chlorided alumina catalysts are useful in the alkylation of paraffins with olefins, as for example the alkylation of isobutane with butene-2 or ethylene, to produce high octane gasoline blending components. Descriptions of chlorided alumina catalysts useful in alkylation are set forth in U.S. Pat. Nos. 3,240,840 and 3,523,142 where the freshly prepared catalyst possesses a high degree of initial activity. Unfortunately, the activity of the catalyst declines after a relatively short period of time on stream and detracts from the commercial attractiveness of an alkylation process employing the same. This decrease in activity or deactivation is related to the concomitant formation of coke which deposits upon the catalyst's surface along with some loss of chlorine associated with the catalyst's active surface. The substantial deposition of coke on the catalyst's surface interferes with the catalytic sites thereby reducing the catalyst's alkylation activity and selectivity leading to a reduction in desired product formation. To partially overcome the deactivating effect of coke upon the catalyst and to maintain the rate of alkylation, more severe alkylation reaction conditions are employed including the use of higher reaction temperatures and the introduction of chloriding agents in the feedstock. Such procedures, while costly, to some extent enables the process to operate on stream for a longer period of time. However, alkylation is preferably carried out at low temperatures to favor conversion and product selectivity and raising reaction temperatures to overcome catalyst deactivation is counter-productive. Ultimately the catalyst will become substantially deactivated by the rising level of coke deposited thereon and continued alkylation only results in diminished conversion and reduced selectivity to desired products.

It is therefore an object of this invention to provide a process for the alkylation of alkanes with olefins employing a regenerated catalyst.

Another object of this invention is to provide an alkylation process employing a regenerated catalyst possessing improved activity and selectivity.

Yet another object of this invention is to provide a method for regenerating a deactivated chlorided alumina alkylation catalyst.

A further object of this invention is to provide a process for the alkylation of alkanes with olefins to obtain high octane gasoline components which process employs a regenerated chlorided alumina catalyst having improved activity and selectivity.

Other objects and advantages will become apparent from a reading of the following detailed description and examples.

SUMMARY OF THE INVENTION

Broadly, this invention contemplates an alkylation process which comprises contacting an alkane and an olefin under alkylation conditions with a regenerated catalyst comprising from about 3.0 to 15.0 weight percent chlorine and alumina, said catalyst having been previously deactivated during use in said alkylation process by the deposition of coke thereupon, and where said regenerated catalyst is prepared by the steps of:

(a) contacting said deactivated chlorided alumina catalyst at a temperature of between 400° and 1200° F. in a non-oxidizing atmosphere;

(b) contacting said catalyst in an oxidizing atmosphere at a temperature between 700° and 1200° F; and (c) rechloriding said catalyst in a non-reducing atmosphere at a temperature between 200° and 800° F.

In another embodiment, this invention contemplates a method for the regeneration of a deactivated alkylation catalyst composed of from about 3.0 to 15.0 weight percent chlorine and alumina and containing coke deposited thereon which comprises contacting said deactivated catalyst at a temperature of between 400° and 1200° F. in a non-oxidizing atmosphere, thereafter contacting the catalyst in an oxidizing atmosphere at a temperature between 700° and 1200° F., and subsequently rechloriding said catalyst in a non-reducing atmosphere at a temperature between 200° and 800° F.

The chlorided alumina catalysts employed in alkylation and regenerated by this invention are derived from known active chlorided alumina catalysts composed of alumina and from about 3.0 to about 15.0 weight percent chlorine. The alumina component may be any of the forms employed in composite catalysts including, for example, eta or gamma alumina. The active chlorided alumina catalyst can be prepared by known methods including contacting alumina with an activator illustrated by carbon tetrachloride, chloroform, methylene chloride, dichlorodifluoromethane, trichlorobromomethane, thionyl chloride or thiocarbonyltetrachloride under non-reducing conditions, that is, under inert or oxidizing conditions where the latter is preferred. Another method of preparing the active catalyst involves contacting alumina with an activator combination of chlorine and hydrogen sulfide or sulfur monochloride or sulfur dichloride, or a combination of chlorine and an organic compound such as tetrachloroethane, tetrachloroethylene, hexachloroethane, pentachloroethane, hexachloroacetone, hexachloroacetone, hexachloro-1,3-butadiene, hexachloropropanone-2, hexachlorocyclopentadiene, hexachloropropylene, trichloroacryloyl chloride, trichloroacetyl chloride, chloral, ethane, ethylene, propane, formaldehyde, methyl alcohol or methyl mercaptan. In general, the known active chlorided alumina catalysts are prepared by contacting alumina with the activator employing temperatures of about 200° to about 800° F., most preferably usually between about 450° and 750° F. The preparation of the chlorided alumina catalysts are described in such U.S. Pat. Nos. 3,240,840, 3,523,142, 3,646,152 and 3,689,434 which are hereby incorporated by reference.

The alkylation catalyst described above is highly active at relatively low alkylation temperatures. Alkane streams composed of n-paraffins or isoparaffins or mixtures thereof are alkylated in the presence of olefins employing the active catalyst at temperatures within the range of about room temperature to about 400° F. and preferably within the range of about 100° to 250° F. Alkylation can be undertaken in either the liquid, vapor or liquid-vapor phase and pressures from atmospheric to the practical maximum limited by the materials of construction can be employed such as up to about 1200 p.s.i.g. Batch or continuous alkylation can be undertaken, the latter employing a liquid hourly space velocity, that is, the volume of liquid alkane charge per hour per volume of catalyst within the range of about 0.5 to 16, preferably within the range of about 4 to 8, being suitable. In general, alkylation proceeds by charging an alkane into the reaction zone together with the olefin with a mole ratio of alkane to olefin within the range of about 100:1 to 2:1, preferably 20:1 to 4:1. The onstream time of the process can be extended by introducing HCl or an HCl precursor such as an alkyl chloride along with the feed, either continuously or by means of periodic introductions. Generally, the HCl is provided in an amount of from about 2 to 2000 ppm by weight based on the olefin feed content.

With regard to the alkylation process a range of alkanes and olefins can be employed. In general, alkanes having from 4 to 10 carbon atoms and preferably from 4 to 6 carbon atoms are employed. Particularly preferred alkanes are the isoparaffins having 4 to 6 carbon atoms. The olefins employed during alkylation include those having from 2 to 6 carbons and preferably those having from 2 to 4 carbon atoms. Suitable alkanes include n-butane, n-pentane, n-hexane, n-heptane, n-octane, n-nonane, n-decane, isobutane, isopentane, isohexane and isoheptane, preferably isobutane or isopentane. Illustrative olefins include ethylene, propylene, butene-1 and -2 and amylene, preferably ethylene or propylene. Highly preferred alkylations include reaction of ethylene with isobutane to form 2,3-dimethylbutane, the reaction of propylene and isobutane or ethylene and isopentane to form 2,2,3-trimethylbutane and the reactions of isopentene and isobutane or isobutene and isopentane or propylene and isohexane to form 2,2,3,3-tetramethylpentane. Other high octane blending components which can be prepared include 2,2-dimethylpentane, 2,3-dimethylpentane, 2,2,4-trimethylpentane, 2,2,3-trimethylpentane, 2,3,4-trimethylpentane, 2,3,3-trimethylpentane and 3,3,5-trimethylheptane. The alkylate may consist of mixtures of isoparaffins of the type mentioned above as for example by the alkylation of isobutane and isopentane with ethylene, propylene, butylene and isobutylene. The alkane charge stocks may be composed of mixtures of alkanes and isoalkanes and the olefin feedstocks may be a mixture of, for example, ethylene and propylene or propylene and butylene.

In the alkylation process described above employing the active chlorided alumina catalyst under alkylation conditions, satisfactory yields of high octane products are recoverable in the early stages of processing. However, prolonged contacting of the reactants and catalyst results in a deactivating amount of coke depositing on the catalyst. Coke laydown on the catalyst seriously affects the process and catalyst deactivation becomes apparent through a decline in alkylate yield along with a loss of selectivity to the desirable products. Catalyst deactivation, whereby activity and selectivity are substantially reduced by the deposition of a deactivating amount of coke on the catalyst, can be observed in some instances after only about 100 hours of processing. For example, in the alkylation of ethylene and isobutane using a 5 weight percent ethylene in isobutane charge blend to provide an iso $C_6$ high octane blending material, after about 100 hours a sharp decline in catalyst activity evidenced in a decline in alkylate yield and selectivity was observed. The conditions employed in the alkylation reaction included temperatures of 200°–250° F., 800 p.s.i.g. and 0.30 LHSV. The following results were observed using a gamma alumina catalyst containing 7.0 weight percent chlorine.

TABLE I

| Time on Stream, Hr. | 8 | 32 | 112 |
|---|---|---|---|
| Alkylate Yield Basis weight % of Olefin Charged | 180 | 179.6 | 80.4 |
| Gas Chromatographic Analysis, Wt.% of Alkylate | | | |
| $C_5$ | 51.8 | 5.9 | 4.7 |
| $C_6$ | 36.9 | 65.6 | 45.0 |
| $C_7$ | 5.7 | 2.4 | 9.0 |
| $C_8$ | 3.3 | 23.9 | 20.2 |
| $C_{9+}$ | 0.2 | 1.8 | 21.1 |
| $C_6$ Composition, Wt.% of Alkylate | | | |
| 2,3-Dimethylbutane | 21.9 | 53.7 | |
| 2- and 3-Methylpentane | 15.0 | 11.9 | |
| $C_8$ Composition, Wt.% of Alkylate | | | |
| 2,2,4-Trimethylpentane | 0.7 | 8.4 | |
| Other C-8's | 2.6 | 15.5 | |
| Bromine Number | 1.0 | 0 | 3.4 |

As can be seen from Table I above, after an on-stream time of 112 hours the chlorided gamma alumina catalyst was substantially deactivated in that the alkylate yield in weight percent decreased from about 180 after 8 and 32 hours to 80.4 after 112 hours. Likewise, the gas chromatographic analysis indicates a substantial decrease in selectivity to the $C_6$ component after 112 hours. The increase in Bromine number signifies that some polymerization is occurring and that olefin is polymerizing rather than alkylating.

REGENERATION

The method for regenerating the deactivated catalyst provided by the instant invention and alkylation processes employing the regenerated catalyst provides a rejuvinated catalyst that is at least as active and in some instances more active than the original fresh catalyst. The results obtained are unexpected inasmuch as the regenerated catalyst possesses a lower surface area than the original fresh catalyst. Chlorided alumina catalysts having high surface areas are generally considered to be highly active and an activity decline is generally associated with lower surface areas. However, it appears that the activity and surface area of the instantly regenerated catalysts may be independent variables inasmuch as the regenerated catalyst while possessing a lower surface area than the fresh catalyst nevertheless has given evidence of increased activity.

In accordance with an embodiment of the invention described herein, regeneration of the catalyst previously deactivated in the course of use in alkylation is undertaken by contacting the deactivated catalyst initially in a non-oxidizing atmosphere at a temperature between 400° and 1200° F., preferably between 500° and 1000° F. The non-oxidizing atmosphere is suitably hydrogen, methane, nitrogen or mixtures thereof, such as hydrogen and methane or hydrogen and nitrogen or hydrogen, nitrogen and methane, preferably hydrogen, and the contacting is conducted at a pressure between about 0 p.s.i.g. and 800 p.s.i.g. where the non-oxidizing atmosphere is preferably introduced as a flowing gaseous stream at a volumetric flow rate of at least 1 and up to 100 standard cubic feet per hour per pound of catalyst for a period of from at least 1 hour and up to 48 hours or longer to remove volatile hydrocarbons sorbed on the catalyst and at least partially crack coke type residues associated on the catalyst's surface. Contacting the deactivated catalyst initially in the non-oxidizing atmosphere under the conditions described above is believed to condition the catalyst's surface for further treatment by reducing the bound hydrogen content of the residues. In the subsequent oxidizing step the presence of bound hydrogen is deleterious in that it promotes the removal of chlorine from the catalyst's surface.

The catalyst is thereafter contacted in an oxidizing atmosphere suitably oxygen, air, or an oxygen containing gas at a temperature between 700° and 1200° F., preferably from about 850° to 1100° F. where the oxidizing atmosphere is preferably introduced as a flowing gaseous stream at a volumetric flow rate of at least 1 and up to 100 standard cubic feet per hour per pound of catalyst for a period of from about at least 1 hour and up to 100 hours or longer. Contacting of the catalyst in the oxidizing atmosphere removes additional and substantial amounts of residue or debris associated with the catalyst's surface. Further, the oxidizing treatment prepares the catalyst's surface for the subsequent rechloriding treatment described below.

In the third step of regeneration, the catalyst following the oxidizing treatment is contacted with a chloriding agent at a temperature of about 200° to about 800° F., preferably between about 450° and 650° F. in a non-reducing atmosphere, that is an inert or oxidizing atmosphere under a pressure of about 0 to 800 p.s.i.g. The rechloriding of the catalyst can be undertaken employing the activator previously described above in connection with the preparation of a freshly prepared active catalyst. Illustratively, rechloriding can be undertaken employing a non-reducing atmosphere while contacting with carbon tetrachloride, chloroform, methylene chloride, dichlorodifluoromethane, trichlorobromomethane, thionyl chloride or thiocarbonyltetrachloride. Alternatively, a combination of chlorine and hydrogen sulfide can be employed or a combination of chlorine and an organic compound such as tetrachloroethane, tetrachloroethylene, hexachloroethane, pentachloroethane, hexachloroacetone, hexachloro-1,3-butadiene, hexachloropropanone-2, hexachlorocyclopentadiene, hexachloropropylene, trichloroacryloyl chloride, trichloroacetyl chloride, chloral, ethane, ethylene or propane can be used. In another embodiment rechloriding can be undertaken by contacting the catalyst in an oxidizing atmosphere and with aluminum chloride. Preferably the rechloriding is undertaken employing an oxidizing atmosphere along with either carbon tetrachloride or aluminum chloride. The rechloriding as described above provides a rechlorination of the catalyst's surface by reacting with exposed hydroxyl groups bared by the cleansing action of the high temperature non-oxidizing and oxidizing treatments undertaken prior to rechloriding. The chlorine content of the regenerated and rechlorided alumina catalyst is in general about the same as that of the fresh catalyst. It is believed, however, that the regenerated catalyst is provided with an improved catalytically active surface essentailly free of surface hydroxyl groups and possesses stronger surface acid sites than the freshly prepared catalyst. Alkylating in the presence of the regenerated catalyst has provided a substantial increase in alkylate yield and an improvement in the selectivity to desired products. Moreover, under similar evaluation conditions wherein alkylations were compared, it was found that the regenerated catalyst while possessing a surface area of about 70 percent of that of the fresh catalyst, nevertheless provided a substantial improvement in alkylate recovery and in selectivity to desired products.

The regenerated catalysts provided by the instant invention can be produced in pellet, granular, bead or pulverulent form to facilitate its use in fixed beds, moving beds or fluidized solid beds as is well known in the art. The catalyst can be regenerated and improved as described herein in situ in an alkylation reactor by passing the various regenerating and improving streams so as to contact the deactivated catalyst under the conditions described herein.

In order to more fully illustrate the nature of our invention and the manner of practicing the same, the following examples are presented.

EXAMPLE I

An active chlorided alumina catalyst was prepared by contacting 490 grams of gamma alumina in a rotary reactor pressured to 30 p.s.i.g. with oxygen and 66.5 grams of carbon tetrachloride at 500° F. for 2 hours at autogenous pressure (about 295 p.s.i.g.). The resulting chlorided alumina catalyst (520 grams) contained 7.3 weight percent chlorine.

The catalyst prepared above (500 grams) was employed in the alkylation of ethylene and isobutane using a 5 weight percent ethylene in isobutane charge blend to provide an iso-$C_6$ high octane blending material. The reaction conditions and results are set forth in Table II after on-stream times of 8 and 144 hours.

After 144 hours on-stream, one-half of the substantially deactivated catalyst was regenerated by contacting with hydrogen (1.0 SCF/hr.) for 2 hours at 700° F., thereafter incrementally at 725° to 900° F. with increasing amounts of air (0.5–5 SCF/hr.) over 8 hours. Thereafter 144 grams of the air burned catalyst was contacted with 14.5 grams of carbon tetrachloride (9.2 cc.) and pressured to 30 p.s.i.g. with oxygen and the reactor heated to 500° F. for 2 hours at a pressure of 145 p.s.i.g. Ethylene-isobutane alkylation was resumed under the origininal conditions described above and the results employing the regenerated catalyst are recorded in Table II. A comparative analyses of the fresh and regenerated catalyst used in this example is shown in Table III.

TABLE II
COMPARISON OF FRESH, DEACTIVATED AND REGENERATED CATALYST

| Chlorided Alumina Catalyst | Fresh | Deactivated | Regenerated |
|---|---|---|---|
| Temp., °F. | 200 | 250 | 250 |
| Pressure, p.s.i.g. | 800 | 800 | 800 |
| LHSV (On Isobutane) | 0.30 | 0.35 | 0.65 |
| Run Time, Hr. | 8 | 144 | 8 |
| Alkylate Recovery, g/1000g Charge | 61.0 | 8.0 | 81.0 |
| $C_5$ and Heavier Alkylate, Wt.% | | | |
| Isopentane | 51.0 | 3.2 | 46.7 |
| 2,3-Dimethylbutane | 21.9* | 6.8 | 31.8* |
| 2- and 3-Methylpentane | 15.0 | 6.5 | 10.2 |
| 2,3-Dimethylpentane | 1.9 | 2.0 | 1.6 |
| 2,4-Dimethylpentane | 3.8 | 5.2 | 3.1 |
| Other $C_7 + C_8$ | 6.3 | — | 8.1 |
| Heavier Than $C_8$ | — | 56.4 | — |

*Increases to about 50 wt.% during the course of the run.

It should be noted that the alkylate yield of 81 grams per 1000 grams of charged stock obtained from the use of catalyst regenerated according to the method of this invention was higher than the yield obtained from fresh catalyst. It should also be noted that the fresh and regenerated catalyst gave about the same product distribution.

TABLE III
PROPERTIES OF FRESH AND REGENERATED CATALYST

| | Fresh | Regenerated |
|---|---|---|
| Chloride, Wt.% | 7.3 | 8.3 |
| Surface Area, m$^2$/g | 243 | 172 |
| Crush Strength, lb.* | 14.8 | 19.1 |
| Carbon, Wt.% | 0 | 0.5 |

*Flat-plate crush strengths.

The catalyst was in the form of 1/16 inch extrudate. While the surface area of the regenerated catalyst is less than the surface area of the fresh catalyst, nevertheless, as reported in Table II above, the regenerated catalyst's activity in alkylation reactions of paraffins with $C_2$-$C_6$ olefins was not adversely affected and indeed a high alkylate recovery of 81.0 grams per 1000 grams of charge was realized as opposed to 61.0 grams per 1000 grams of charge when fresh catalyst was employed.

We claim:

1. In an alkylation process wherein an alkane and an olefin are contacted under alkylation conditions at a mole ratio of alkane to olefin of about 100:1 to 2:1 with an active catalyst consisting essentially of from about 3.0 to 15.0 weight percent chlorine and alumina and where said catalyst is deactivated during use in said alkylation process by the deposition of coke thereupon, the improvement which comprises regenerating said catalyst by the steps of:
    (a) contacting said deactivated chlorided alumina catalyst at a temperature of between 400° and 1200° F. in a non-oxidizing atmosphere, wherein said non-oxidizing atmosphere is hydrogen, methane, nitrogen or mixtures thereof;
    (b) contacting said catalyst in an oxidizing atmosphere at a temperature between 700° and 1200° F., wherein said oxidizing atmosphere is oxygen, air or an oxygen-containing gas; and
    (c) rechloriding said catalyst in a non-reducing atmosphere at a temperature between 200° and 800° F. by contacting said catalyst with a conventional chloriding alumina activating agent and chloriding said catalyst to about 3.0 to 15.0 weight percent chlorine, wherein said non-reducing atmosphere is an inert or oxidizing atmosphere, wherein said alumina is gamma alumina and wherein said regenerated catalyst possesses an alumina surface area substantially reduced from that of said active catalyst.

2. A process according to claim 1 wherein said non-oxidizing atmosphere in (a) is hydrogen.

3. A process according to claim 1 wherein said contacting in (a) is at between 500° and 1000° F.

4. A process according to claim 1 wherein said contacting in (a) is at a pressure of between about 0 and 800 p.s.i.g.

5. A process according to claim 1 wherein said contacting in (b) is from about 850° to 1100° F.

6. A process according to claim 1 wherein said rechloriding in (c) is undertaken by contacting with carbon tetrachloride.

7. A process according to claim 1 wherein said rechloriding in (c) is undertaken by contacting with aluminum chloride.

8. In a method for the regeneration of a deactivated chlorided alumina alkylation catalyst consisting essentially of from about 3.0 to 15.0 weight percent chlorine and alumina, said deactivated catalyst derived from the alkylation of an alkane and an olefin under alkylation conditions at a mole ratio of alkane to olefin of about 100:1 to 2:1 with an active chlorided alumina alkylation catalyst and where said active catalyst is deactivated during use in said alkylation process by the deposition of coke thereon which method comprises contacting said deactivated catalyst at a temperature of between 400° and 1200° F. in a non-oxidizing atmosphere, wherein said non-oxidizing atmosphere is hydrogen, methane, nitrogen or mixtures thereof, thereafter (b) contacting said catalyst in an oxidizing atmosphere at a temperature between 700° and 1200° F., wherein said oxidizing atmosphere is oxygen, air or an oxygen-containing gas, and subsequently (c) rechloriding said catalyst in a non-reducing atmosphere at a temperature between 200° and 800° F. by contacting said catalyst with a conventional chloriding alumina activating agent and chloriding said catalyst to about 3.0 to 15.0 weight percent chlorine, wherein said non-reducing atmosphere is an inert or oxidizing atmosphere, wherein said alumina is gamma alumina and wherein said regenerated catalyst possesses an alumina surface area substantially reduced from that of said active catalyst.

9. A method according to claim 8 wherein said non-oxidizing atmosphere in (a) is hydrogen.

10. A method according to claim 8 wherein said contacting in (a) is at between 500° and 1000° F.

11. A method according to claim 8 wherein said contacting in (a) is at a pressure of between about 0 and 800 p.s.i.g.

12. A method according to claim 8 wherein said contacting in (b) is from about 850° to 1100° F.

13. A method according to claim 8 wherein said rechloriding in (c) is undertaken by contacting with carbon tetrachloride.

14. A method according to claim 8 wherein said rechloriding in (c) is undertaken by contacting with aluminum chloride.